United States Patent
Mueller et al.

(10) Patent No.: US 9,119,892 B2
(45) Date of Patent: Sep. 1, 2015

(54) PROCESS FOR TEXTILE CLEANING AND DISINFECTION BY MEANS OF PLASMA AND PLASMA LOCK

(75) Inventors: Siegfried Mueller, Greifswald (DE); Rolf-Juergen Zahn, Greifswald (DE); Wolfgang Reich, Griefswald (DE); Klaus-Dieter Weltmann, Ostseebad Binz (DE); Kirsten Anklam, Bremerhagen (DE); Diana Neudeck, Greifswald (DE); Tila Krueger, Guetzkow (DE); Norman Mleczko, Neumuenster (DE); Torsten Koburger, Greifswald (DE); Ivonne Harfenstein, Greifswald (DE)

(73) Assignee: Leibniz-Institut fuer Plasmaforschung und Technologie e.V., Greifswald (DE)

( * ) Notice: Subject to any disclaimer, the term of this patent is extended or adjusted under 35 U.S.C. 154(b) by 260 days.

(21) Appl. No.: 12/672,953
(22) PCT Filed: Aug. 8, 2008
(86) PCT No.: PCT/EP2008/060453
§ 371 (c)(1), (2), (4) Date: Feb. 10, 2010
(87) PCT Pub. No.: WO2009/021919
PCT Pub. Date: Feb. 19, 2009

(65) Prior Publication Data
US 2012/0111359 A1 May 10, 2012

(30) Foreign Application Priority Data
Aug. 10, 2007 (DE) .......... 10 2007 037 984

(51) Int. Cl.
A61L 2/10 (2006.01)
A61L 2/14 (2006.01)
(Continued)

(52) U.S. Cl.
CPC . *A61L 2/202* (2013.01); *A61L 2/10* (2013.01); *A61L 2/14* (2013.01); *A61L 9/015* (2013.01);
(Continued)

(58) Field of Classification Search
None
See application file for complete search history.

(56) References Cited

U.S. PATENT DOCUMENTS

| 2,978,066 A | 4/1961 | Nodolf |
| 3,509,696 A | 5/1970 | Thompson |

(Continued)

FOREIGN PATENT DOCUMENTS

| DE | 30 04 474 | 8/1981 |
| DE | 32 48 590 | 8/1983 |

(Continued)

*Primary Examiner* — Nicole Blan
(74) *Attorney, Agent, or Firm* — Jordan and Hamburg LLP

(57) ABSTRACT

A process and apparatus for cleaning and disinfection of textiles and the air from viruses, bacteria and spores, and also for purifying from dust, pollen, odors, etc. in which the employment of water and various other cleaning agents and disinfectants as well is not required includes a lock or chamberin which living beings are able to stay, and piece-goods and textiles, etc. are able to be treated as well. Therein, airborne aerosols (droplets, particles, dust) as well as aerosols and microbes, respectively, adhering to the clothing or body and to the product, respectively, are to be treated. The basic principle shall also be applicable to rooms (e.g. waiting rooms) or stables and under cleanroom conditions as well. Various aspects of the invention include plasma generation, producing an ion current from the plasma, ozone generation and activation, sterilization, oxidation and decomposition of gaseous components, and separation of microbes and aerosols and decomposition thereof.

9 Claims, 6 Drawing Sheets

(51) Int. Cl.

| | | |
|---|---|---|
| *A61L 2/20* | (2006.01) | |
| *A61L 9/015* | (2006.01) | |
| *A61L 9/20* | (2006.01) | |
| *A61L 9/22* | (2006.01) | |
| *D06L 1/00* | (2006.01) | |
| *D06L 3/00* | (2006.01) | |
| *D06L 3/04* | (2006.01) | |
| *D06M 10/00* | (2006.01) | |
| *D06M 10/02* | (2006.01) | |
| *D06M 10/06* | (2006.01) | |
| *D06M 16/00* | (2006.01) | |

(52) U.S. Cl.
CPC ... *A61L 9/20* (2013.01); *A61L 9/22* (2013.01); *D06L 1/00* (2013.01); *D06L 3/00* (2013.01); *D06L 3/04* (2013.01); *D06M 10/001* (2013.01); *D06M 10/025* (2013.01); *D06M 10/06* (2013.01); *D06M 16/00* (2013.01); *A61L 2202/25* (2013.01); *A61L 2202/26* (2013.01)

(56) References Cited

U.S. PATENT DOCUMENTS

| | | | |
|---|---|---|---|
| 4,550,578 A | 11/1985 | Sando et al. | |
| 5,960,648 A | 10/1999 | Straemke | |
| 6,451,252 B1* | 9/2002 | Ruan et al. | 422/22 |
| 2003/0029566 A1* | 2/2003 | Roth | 156/345.35 |
| 2003/0030374 A1* | 2/2003 | Pai | 313/582 |
| 2004/0120845 A1 | 6/2004 | Potember et al. | |
| 2005/0001527 A1* | 1/2005 | Sugiyama | 313/231.31 |
| 2005/0161433 A1* | 7/2005 | Silberberg et al. | 216/67 |
| 2006/0096331 A1 | 5/2006 | Kim | |
| 2006/0260065 A1* | 11/2006 | Wright et al. | 8/158 |
| 2007/0253860 A1 | 11/2007 | Schroder | |

FOREIGN PATENT DOCUMENTS

| | | |
|---|---|---|
| DE | 3420973 | 12/1985 |
| DE | 43 39 611 | 10/1994 |
| DE | 196 34 725 | 3/1998 |
| DE | 197 17 890 | 4/1999 |
| DE | 198 26 831 | 10/1999 |
| DE | 100 57 862 | 2/2002 |
| DE | 102 45 902 | 4/2004 |
| DE | 103 44 489 | 4/2005 |
| DE | 10 2005 003 923 | 4/2006 |
| DE | 10 2005 035 951 | 2/2007 |
| DE | 603 07 062 | 2/2007 |
| JP | 2005-224757 | 8/2005 |
| WO | WO- 2005/028081 | 3/2005 |

* cited by examiner

PROCESS FOR TEXTILE CLEANING AND DISINFECTION BY MEANS OF PLASMA AND PLASMA LOCK

BACKGROUND OF THE INVENTION

The invention relates to a process for textile cleaning and disinfection by means of plasma representing a new way towards a waterless washing machine. Furthermore, the invention relates to a lock or room for inactivating viruses, bacteria and spores, and also for purifying air in the conventional sense such as from dust, pollen, odors or the like.

There are various dangers to health, e. g., caused by polluted air. In addition to gaseous components and aerosols of anthropogenic origin, in particular biological components such as viruses, spores, bacteria or pollen. Viruses and bacteria can be transmitted from contaminated areas through living beings, vehicles or parcels. Recently, virological dangers such as H5N1 (bird flu), influenza or SARS mainly became the focus since there's risk of pandemics. In the normal case, for infection a sufficiently high concentration of the infectious matter is required.

Apart from the indoor air or ambient air, often exhaust gases or waste air carry microorganism strains which are harmful for health and environment. In many cases, the exhaust gases or the waste air are repeatedly charged with aerosols. These can additionally be the carriers of disturbing odors or volatile organic compounds (VOCs). VOC is to be understood as harmful hydrocarbon compounds.

Aerosols is the generic term of solid and liquid particulates. In particular, smaller aerosols in the range of a few nanometers are especially harmful. These impurities often indicated as nanoparticulates are able to uncheckedly enter into the human lungs, or even to immediately be assimilated through the skin. The most known example of such nanoparticulates is the particulate matter in diesel exhaust gases. Further, in the indoor air often harmful substances such as particulates of cigarette smoke, toner of photocopiers or paper dust of copy paper are contained.

Various measures are taken in order to reduce concentrations of microorganism strains in the exhaust gases or waste air. Conventional means such as mechanical separators, mechanical filters, gas washers or combustion are only in a limited use, are too costly or consume too much energy.

Specially for the separation of aerosols, and in particular the removal of macroscopic dust particles from industrial exhaust gases electrostatic filters or even electrostatic precipitators for the purification are known. This process also being referred to as electrical gas scrubbing includes electric charging of dust particles with corona discharge as a standard step. A typical geometry consists of a thin wire which is enclosed by a cylinder spaced from the wire. According to polarity of the wire electrode a distinction is made between negative corona and positive corona. With the negative corona, the electron attachment results in the generation of negative ions attaching to aerosols as the case may be. Sometimes, this process is also described as the ion blow.

The electrostatic precipitators comprise so called collecting electrodes and discharge electrodes with appropriate high-voltage fields between them. The dust particles collected on the collecting electrode are mechanically removed which is disadvantageous in certain applications. Also, the high voltages of several 10 kilovolts required for the electrostatic precipitators are disadvantageous.

In DE 34 20 973 A1 there is proposed a combination including filter mats on which the removed dust can be collected.

In DE 102 45 902 A1 the collecting electrode includes a space into which the particles are able to enter and inside of which no potential difference is prevailing.

In DE 30 04 474 C2 the corona-starting voltage below flashover voltage is superimposed by a pulse voltage having pulse widths ranging from ns to ms.

According to DE 43 39 611 A1, charging of dust particles in the entire volume, a homogeneous collection surface and prevention of electric disruptive discharges shall be achieved in that a segmentation is taking place in the flow direction in which dielectric barrier discharge paths for charging dust particles alternate with "normal" collecting paths having high homogeneous electric fields between metallic electrodes. The dielectric barrier discharge is operated between a dielectric diode and the collecting electrode, thus over the entire cross-section of the gas space. As a result, in this configuration very high voltages (alternating voltages in this case) are required similar to corona discharge, with a greater exhaust passage to achieve a small flow resistance. The common problems continue to exist for the corona portion.

Generally, it is also known that the most different chemical reactions which mainly proceed through very reactive species, so called radicals, can be initiated with plasmas. This has been analyzed and used for various applications of treating exhaust gases or even for plasma-chemical reactors. Then, solutions have been proposed which make use of dielectric barrier discharge for generating appropriate plasmas. Dielectric barrier discharges (hereinafter also DBDs) are characterized in that at least one of the conductive electrodes is provided with a dielectric thus forming an insulated electrode, or in that a dielectric is disposed between the conductive electrodes. The configuration of such arrangements can be multiform. Depending on this configuration and the remaining parameters specific characteristics of the DBD are often achieved. Sometimes, specific designations are used according to such configurations or according to the purpose of application (e.g. ozonizer).

Generally, the DBD can be operated with sinusoidal or square-wave AC voltages ranging from a few Hz up to several hundreds of kHz. Various embodiments of the DBD are known as a discharge configuration. Frequently, with the large-area electrodes, a plurality of small discharge threads also called filaments having a thickness of up to a few of tenths of millimeters and being statistically distributed for the most part are provided. In the transition region toward the insulated electrodes these filaments form spreadings which frequently pass over to surface gliding discharges having a plurality of further thin discharge channels.

Such phenomena of surface gliding discharge are able to be dominant in specific arrangements, so called coplanar discharge arrangements or surface discharge arrangements. It is also known that, in particular in gas fillings with inert gases and in thereof mixtures, respectively, discharge structures can be formed which are not filamented. Besides, various combinations and transient modifications of discharge embodiments are possible.

With reactors assembled according to the prior art in particular, aerosols cannot really be retained and decomposed within the plasma.

According to DE 197 17 890 C1, it is provided for an effective treatment of soot particles to collect particulate matter on a porous filter element and to expose it to the plasma of a DBD. A similar principle is indicated in DE 100 57 862 C1. With this principle, however, the problem of ash deposition and blockage continues to exist.

It is known from WO 2005/028081 and DE 103 44 489 A1, respectively, that a contiguous electrode being structured toward all directions in space is used, wherein insulating material is placed on the elevations thereof. This insulating material forms a delimiting face for the structured electrode. On the other side of the insulating material an additional electrode is mounted. The structured electrode consists of a wire mesh, contiguous or adjacent solids and structures, respectively, made of an electrically conductive material. At the same time, the structured electrode simultaneously functions as a spacer for additional plane surfaces and as a filter element. The discharge representing a specific configuration of a DBD develops in the clearances of the electrode structure and on the surface of the insulating material.

For some applications, the structure provides an excessive back pressure. In addition, the reactions within the plasma are often highly complex since all species generated within the plasma are able to be involved in the reactions.

An arrangement according to DE 198 26 831 A1 is further known wherein the plasma reactor consists of a tubular electrode which is coated with a dielectric barrier on its inner surface. A conductive electrode facing the gas space and made of a wire mesh, for example, is mounted as a counter electrode being in contact with the barrier. With appropriate voltages, it then results in the development of gas discharges within the gap area of the wire screen electrode and the dielectric barrier. Mixing the influent gas and the plasma region is carried out by means of vortex effects in the immediate area of the wire screen electrode.

In DE 196 16 206 A1 gas discharge is mainly generated on the surface of a dielectric wherein the electrode facing toward the gas provides an immediate contact with the dielectric and consists of thin bar stock having a rounded cross-section. Catalytically acting materials are located in a distance of some millimeters toward this electrode facing the gas, and are at the same potential.

With these arrangements, the restricted exchange between the plasma and remaining gas has an adverse effect on many applications and as a result on the plasma-induced reactions within the gas as well. Further, aerosols or soot particles cannot be separated since any filtering or separation is not available. Subsequently, in the plasma of such arrangements the aerosols/soot particles will not successfully be decomposed with it as well.

Applicants have provided an arrangement and method wherein plasma is generated with a dielectric barrier discharge arrangement within a large area region wherein an open structure of the DBD toward the face of the gas space for the influent gas is available. According to the method, ions are extracted from the plasma of DBD and accelerated in an electric field such that an ion blow covering the space for the influent exhaust gas and the waste air, respectively, is generated. In a simple embodiment, the electric field is developed for ion extraction by means of negative pulse voltages of the plasma generating portion of a dielectric barrier discharge. The face of the device opposing this DBD arrangement is at ground potential. Negative ions are accelerated toward the ground potential such that aerosols contained in the gas can be charged and separated. In another embodiment then, in addition to the separation of aerosols, the decomposition thereof within the plasma is also provided. For that, opposite dielectric barrier discharge arrangements are formed. The faces of the DBD arrangements opposing each other toward the gas space for the influent gas are then applied with positive and negative pulse voltages, respectively. In this way, charge carriers as well as charged aerosols drift, depending on the sign of the charge thereof, towards the electrode of the DBD each conducting opposite potential. There, the aerosols are separated and decomposed in the plasma of the respective DBD.

Such systems, in al., generate ozone such that a longer presence of living beings in such rooms or spaces is not possible.

Previous disinfection systems and air purification systems have different operation limits. Systems based on plasmas operate according to the air recirculation principle or the injection principle. Then, the room air including its harmful constituents is essentially treated by reactive species within the reactor portion. In another case, reactive constituents from a plasma unit are added into the room (such as with the disinfection by means of ozone). Such systems are only applicable to some extent, and only gaseous or gasborne constituents can be treated this way. It is also critical to observe treatment times (and so retention time) regarding the disinfection.

A very effective method of disinfection/air purification is provided with UV methods. At the same time, however, direct disinfection is only possible only without exposure of people. Also, recirculation mode and indirect disinfection are possible, but including similar problems as before.

With the routine disinfection including disinfectants, considerable losses of effectiveness at a falling temperature occur such that the pass-through vessels or epidemic or disease mats will be restricted in their effectiveness. Further, these means are not allowed to be directed to unprotected persons.

Cleaning and disinfection of textiles are connected with the employment of water and various cleaning agents and disinfectants as well. This requires a considerable consumption of our water resources resulting in varied water pollutions. Then, expensive sewage treatment processes are necessary.

The object and pollution level as well as the nature of pollution are very different. So, the whole panoply of applications is ranging from simple clothing up to cleanroom drapery, medical textiles or even protection equipment. The nature of pollution shows a still wider range. This extends from simple odor load of clothes beyond the pollution with bio-aerosols (microbes, spores, pollen) up to various other pollutions.

Treatment of textile fabric by means of plasma is known from the patent publications DE 19634725 A1 and DE 3248590 A1. Herein, the surfaces of textiles are treated in such a manner that with later necessary cleaning less power and water are needed. Complete cleaning by means of plasma is not carried out.

In JP 2005224757 A is disclosed a possibility of the surface cleaning of textiles by means of plasma. The plasma cleaning device is to save chemicals and cleansing agents, and comprises an iron having a water tank and plasma electrodes for plasma generating at a standard pressure. The water vapor is guided through the plasma wherein hydroxyl radicals are developed which clean the textiles.

Furthermore, there are devices by means of which the polluted air is disinfected through a UV unit and an ionisation unit. Known devices are described in DE 102005003923 A1 and in DE 102005035951 A1. Basically, with the employment of ultraviolet radiation and use of ozone connected therewith the following reaction mechanisms are known. Molecular oxygen ($O_2$) is decomposed into oxygen radicals. The so developed oxygen radicals react themselves again with molecular oxygen during the formation of ozone. Under the influence of ultraviolet light the ozone being so developed can be decomposed into oxygen radical and molecular oxygen again. The oxygen radical is now available in order to react with water to two hydroxyl radicals or with molecular oxygen to ozone again.

Application for cleaning textiles is not provided herein.

SUMMARY OF THE INVENTION

It is an object of the invention to develop a process for cleaning and disinfection of textiles, wherein the employment of water and various cleaning agents and disinfectants as well is not required and can significantly be reduced, respectively. Furthermore, it is an object to develop a lock for inactivating viruses, bacteria, spores and for cleaning air in a conventional sense such as from dust, pollen, odors, etc. as well. In the lock, living beings should be able to stay, and piece-goods and textiles, etc. should be able to be treated as well. As a result, airborne aerosols (droplets, particles, dust) as well as aerosols and microbes, respectively, adhering to the clothing or to the body and the product, respectively, are to be treated. The basic principle shall also be applicable generally to rooms (e.g. waiting rooms) or stables as well as under cleanroom conditions.

According to the invention, cleaning of odor loaded clothing, e.g., and the disinfection of textiles as well is carried out on the basis of plasma processes. Then, the following steps are used:
  a) Plasma generation,
  b) Ozone generation and activation,
  c) Sterilization,
  d) Oxidation and decomposition of gaseous components,
  e) Separation of microbes and aerosols, and
  f) Decomposition thereof Plasma generation is used from which ions can be extracted through pulse voltages of different sign. In one embodiment positive or negative ions are alternately extracted.

Oxygen activation is carried out by means of ultraviolet radiation in the reaction chamber.

Sterilization is carried out by means of one or a plurality of the following components such as generated ozone, active oxygen, extracted ions and ultraviolet radiation.

Plasma generation is carried out such that an injection of ozone and of reactive species (radicals) into the reaction chamber is enabled.

Microbes and aerosols are electrically charged by means of extracted ions, and thus are fed through an electric field into a separation area or a plasma unit for decomposition.

Gaseous components such as odorous substances are oxidized and/or decomposed by means of generated ozone, active oxygen, extracted ions and ultraviolet radiation in the reaction chamber.

Mechanical means such as ventilation or beating as well as turnover devices are provided to support the effectiveness of cleaning.

In contrast to conventional processes such as for example conventional washing, chemical cleaning/disinfection, chemical bleaching including chlorine, the advantages are in the simplicity and the low effort. Water as well as cleansing agents and disinfectants and chemicals can be saved in considerable extent during cleaning of germ-infested textiles, adhering odors and pollutions because of dust aerosols, spores, and pollen as well are to be removed.

The object is solved by means of processes for the ion generation and ion extraction (ionic wind—transportation of the ions into the treatment room or chamber), further through charging and separation of aerosols/microbes or the attachment of ions, and the decomposition/oxidation of microbes/ aerosols through ion-molecular reactions. A special combination with known sterilisation processes is provided as a further component in the process.

The important benefit is in the great social significance as to the health. The process avoids great economic damages in agriculture. Further, industrial processes will be enabled or be improved.

BRIEF DESCRIPTION OF THE DRAWINGS

The invention will be explained in the light of embodiments. Herein.

DETAILED DESCRIPTION OF THE INVENTION

Plasma generation/ozone generation and activation

Energy-efficient processes and arrangements for the plasma generation and of subsequent reactions (oxidation) will be demonstrated. In particular, a high reactivity will be achieved by parallel activating of ozone with the radiation through ultraviolet light such that atomic oxygen is resulting from it. This is particularly reactive.

Figure 1:
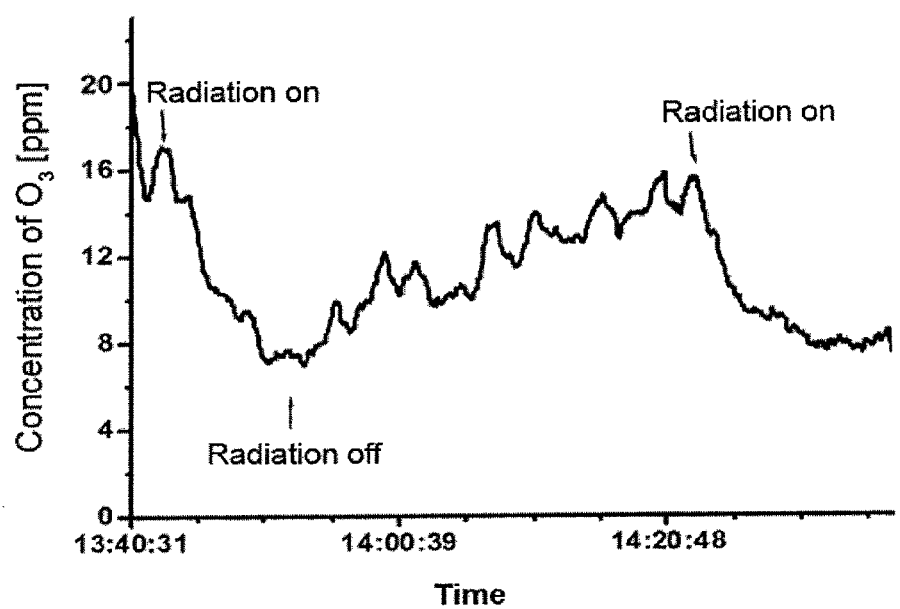
FIG. 1 shows the oxygen activation through radiation of ozone.

FIG. 1 shows the rapid decrease of the ozone concentration shortly after the beginning of radiation by means of ultraviolet light. If the ultraviolet light is again switched off, then the ozone concentration is increasing again.

Disinfection

Two effective processes for the disinfection have been developed. With the textile structures being particularly complicated for the cleaning processes they have succeeded in a 5-log germ reduction of test textiles provided with bacteria $E.\ coli$, and a 7-log germ reduction with aerosols (from $10^7$ microbes to "not detectable").

Then, the textiles are exposed to the plasma in the varying process arrangements, wherein the ion blow as well as ozone and secondary reactions and short living species are used as well.

Figure 2:
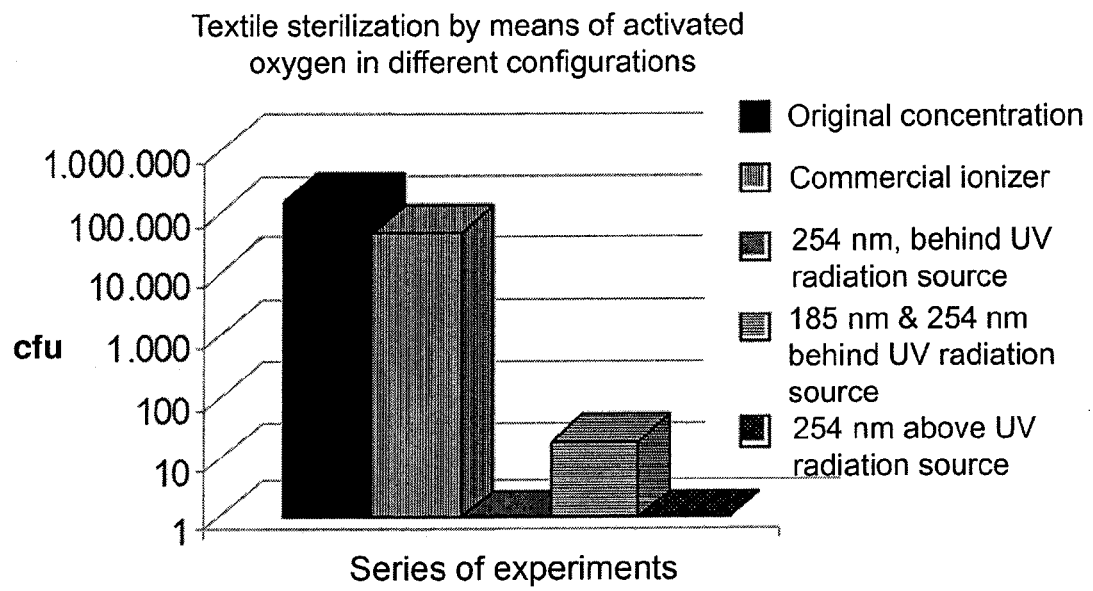
FIG. 2 shows textile disinfection by means of activated oxygen in various arrangements.

FIG. 2 shows the textile disinfection by means of activated oxygen in various arrangements. The duration of the tests amounted to 2 times 15 min. As a result, it will be appreciated from the graph that alterations could hardly be noticed with the use of a commercial ionizer. It has turned out that the radiation with a UV source having a wavelength of 254 nm is providing the most effective results, it makes no difference whether this source is placed in front of or beneath the material.

Figure 3:
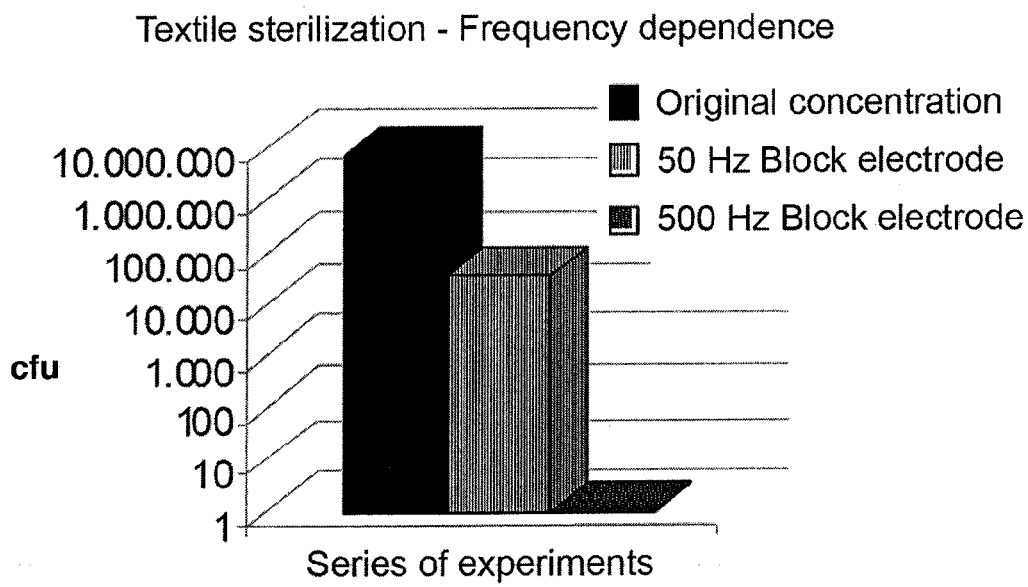
FIG. 3 shows textile disinfection—frequency dependence.

FIG. 3 shows the textile disinfection with block electrodes of different frequencies. Here, the duration of the test also amounted to 2 times 15 min. The evaluation indicates that there is only low disinfection at 50 Hz, however, any microbes essentially cannot be detected any more at a frequency of 500 Hz.

Oxidation and decomposition of gaseous components

In the case of gaseous components adhering to the clothes, it has been demonstrated with the elimination of kitchen odors that elimination below a burdensome odor threshold is attained. So, the aldehydes and MEK (reference substance for kitchen odors), for example, have been decomposed.

Figure 4:
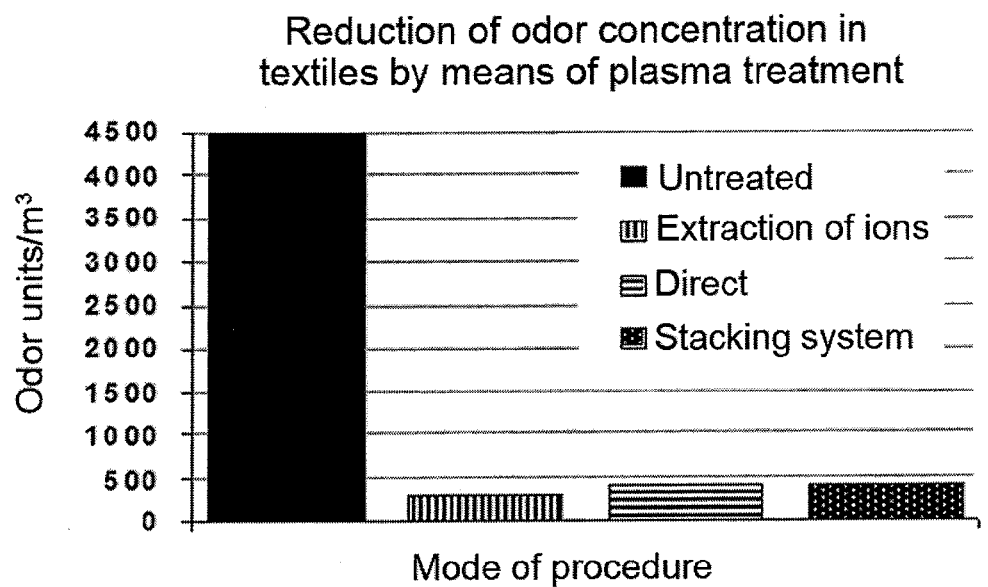
FIG. 4 shows the reduction of odor concentration in textiles by means of plasma treatment.
Figure 8:
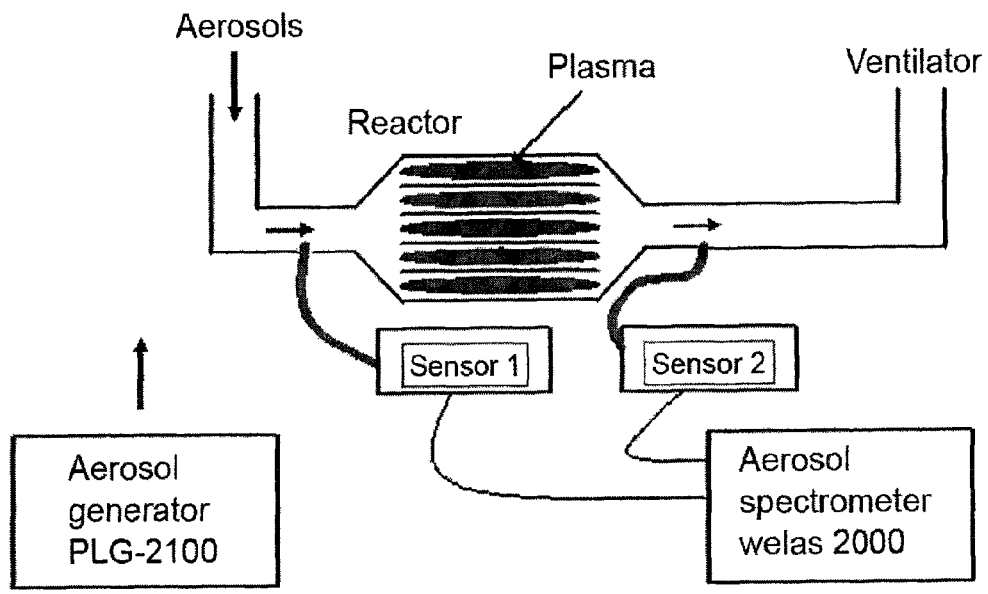
FIG. 8 shows a schema of the plasma treatment in the stack system reactor.

FIG. 4 shows a graph in which the reduction of the odor concentration in textiles by means of plasma treatment is illustrated. The odor units per $m^3$ amount to 4500 when untreated. The best results have been measured after treating with an ion extraction. Similarly, with the direct plasma treatment and treatment in the stack system as shown in FIG. 8, values below 500 odor units per $m^3$ have been measured.

Figure 10:
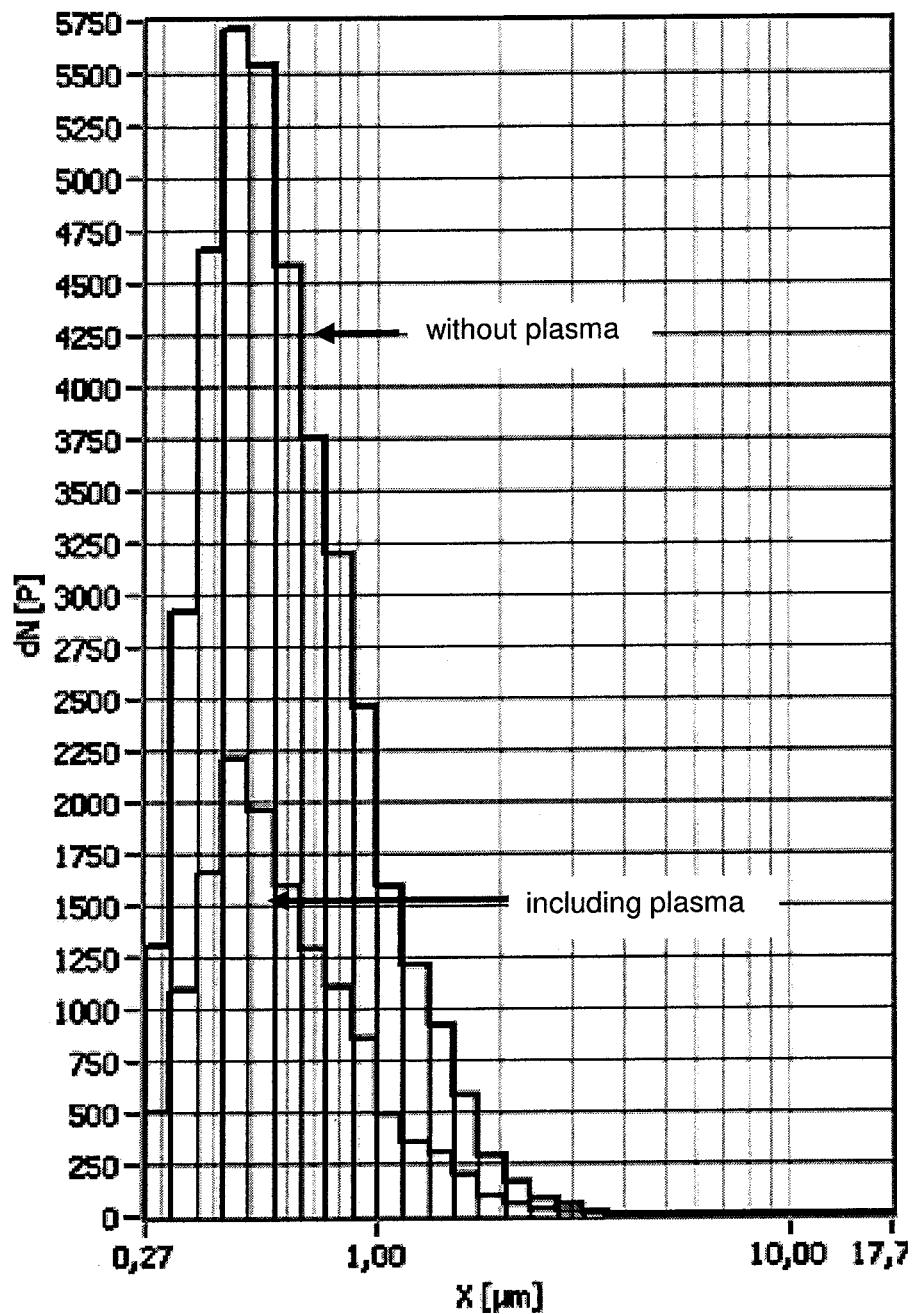
FIG. 10 shows a graph of the comparison between without plasma (blue) and including plasma (red) in the stack system reactor (stacking system with 50 grids).

For this purpose, in FIG. 10 is illustrated a graph of the comparison between without plasma and including plasma, in the stack system reactor (stacking system with 50 grids).

Separation of Microbes and Aerosols and the Decomposition Thereof

The aerosol separation and decomposition is another essential feature of the present process. This is enabled by a novel principle for the ion extraction from plasma. Contaminant particles up to bio-aerosols can be charged and subsequently be separated with that in quite short time intervals, and supplied to another plasma for decomposition again, respectively.

In special arrangements, the specified elements allow cleaning of odor loaded clothes as well as the disinfection and bleaching of whites.

The proposed principle presents itself a plurality of further possibilities of the application.

Textile cleaning (at the moment odors easily polluted) in the home area,
  Cleaning of cleanroom textiles,
  Cleaning of medical textiles,
  Cleaning of protection equipment,
  Cleaning of clothes for allergy sufferers (lock, closet)

Customer's benefit is particular in dry textile cleaning. The expensive washing and drying operation and partly the ironing operation are omitted.

Figure 5:
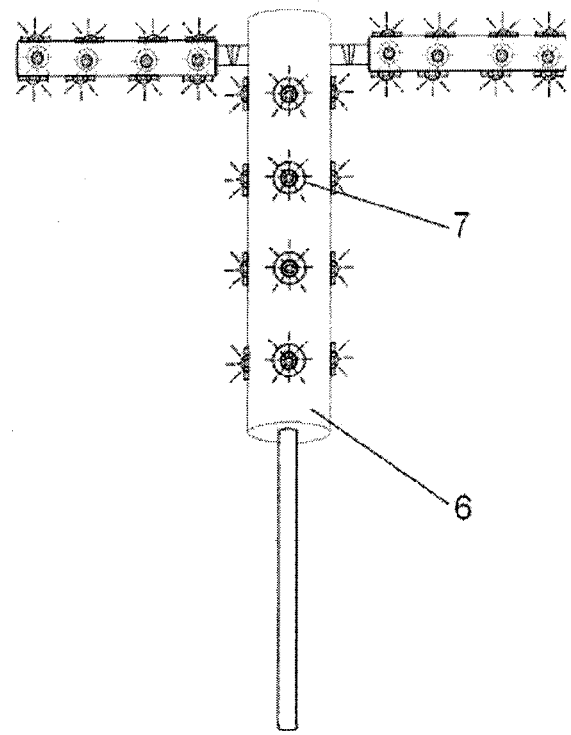
FIG. 5 shows a device for cleaning of easily contaminated or odor loaded textiles.

In FIG. 5 a device is illustrated by means of which easily polluted or odor loaded textiles can be cleaned. The device comprises a body 6 having nozzles 7. The body 6 is hollow and appropriate for the cross-flow of air exiting then through the nozzles 7. The clothes to be cleaned can be hung over this body. Inside of the body an electrode system for the generation of plasma is disposed. Preferably, the electrode system is a form of dielectric barrier discharge. There in the plasma, the reactive species such as ozone will be generated which flow through the nozzles then. For the enhancement of effectiveness, within the nozzles the ozone will be photolytically decomposed with ultraviolet light and changed into molecular and atomic active oxygen which is particularly reactive.

Figure 6:
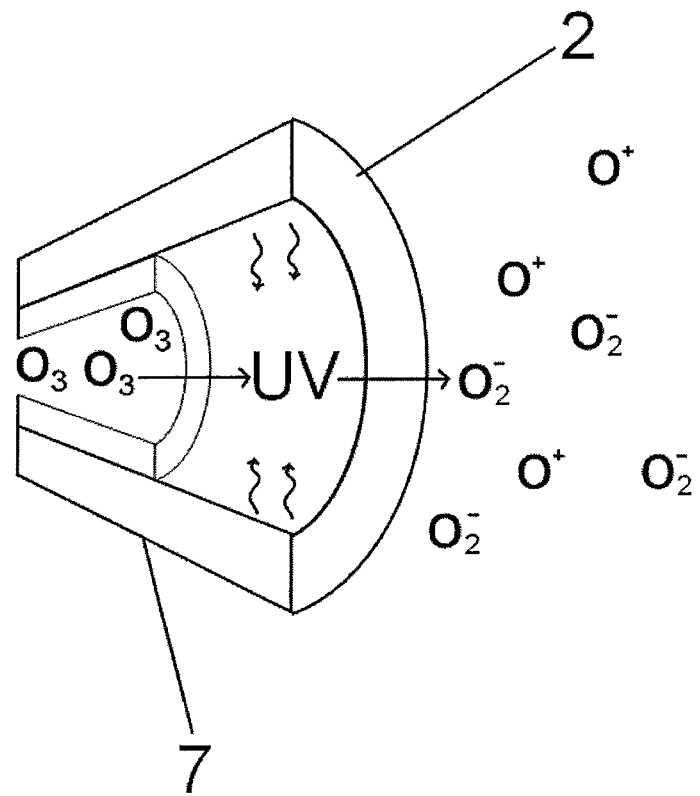
FIG. 6 shows the diagrammatic mode of operation of the nozzle.

FIG. 6 schematically illustrates the mode of operation of the nozzle. By arranging the UV source within the nozzle and in its vicinity, respectively, it is assured that the active oxygen is lasting long enough in order to be able to be used for cleaning purposes.

Figure 7:
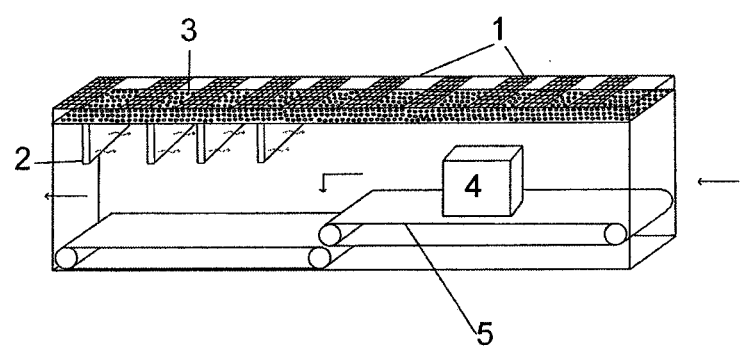
FIG. 7 shows an arrangement formed as a lock.

FIG. 7 shows an arrangement which is formed as a lock. In the roof of the lock there are disposed electrode systems 1, preferably being configurations of surface discharge by means of which ions can be extracted through pulse voltages from the discharge area. It is provided for this process that the polarity of the pulse voltage is changing from time to time in order to avoid one-sided charging of the material located in the lock. Below the electrode system there is located an orifice grid 3 for the extraction of ions. The orifice grid 3 is allowed to have other shapes as well such as, for example, tightened wires or wire netting. Shutters serving as high voltage lenses can also be employed.

In one embodiment, the orifice grid 3 or wires can be enclosed with insulating material to avoid undesired draining off of ions.

In the embodiment according to FIG. 7 a piece-good 4 is shown. This shall be moved through a conveyor 5 such that, if possible, the entire surface is exposed to the plasma and to the extracted ions. An ultraviolet light source 2 is provided to improve the effectiveness. The ultraviolet light source 2 may be, for example a flat excimer lamp which is filled with KrCl, for example, and emitting an ultraviolet wavelength of 220 to 230 nm or an ultraviolet light source filled with of XeCl and having a wavelength range of 290 to 315 nm. Other lamps working in this wavelength range can also be employed such as, for example, mercury vapor lamps having a wavelength of 254 nm.

Figure 9:
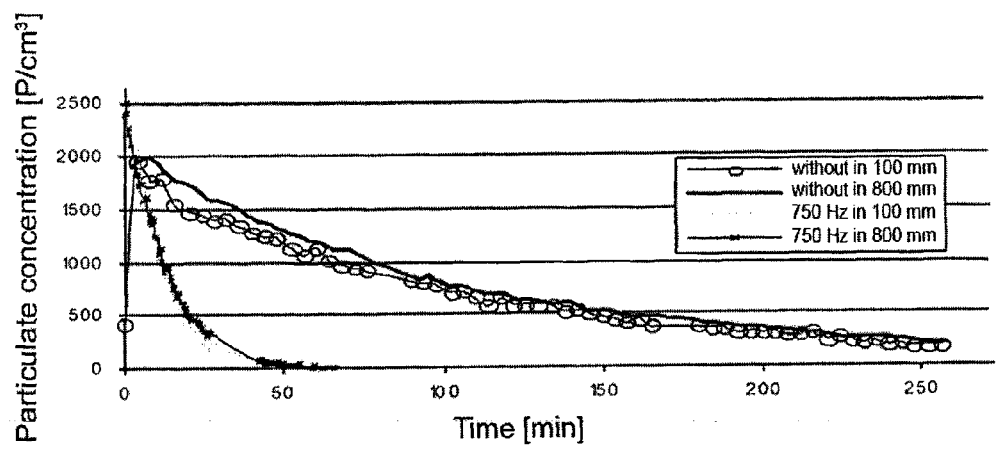
FIG. 9 shows a diagram of particle concentration vs. time.

FIG. 9 shows the decrease of particle concentration per $m^3$ compared with the time. At a frequency of 750 Hz, no particles are detectable any longer after approximately 50 min.

Application is not restricted to the lock or chamber for piece-goods. So, there you can pass through various textiles in particular cleanroom textiles, medical textiles, protective clothing or even clothes for allergy sufferers.

In a specific arrangement even direct access of such a lock to people is provided. This is particularly advantageous for allergy sufferers.

The plasma lock is applicable in or behind/in front of spacious passenger transport systems such as airplanes, railroad, ships and infested areas as well.

Moreover, the principle is applicable to health devices such as clean air blankets, sterile cabins (access including lock again), livestock breeding/stables. Further possible areas are: food industry, semiconductor industry, optics area; the home area (allergies), hothouses and storage for fruits, vegetables and cereals as well are also conceivable.

The invention claimed is:

1. A process for cleaning and disinfecting an object contaminated with microbes and infectious aerosols comprising the steps of placing a contaminated object in a chamber having a size sufficient to receive an object large in size, generating a plasma, the plasma being generated at a location that does not provide direct exposure of the plasma to the object, extracting ions from the plasma by generating alternating positive and negative pulse voltages in the plasma, whereby positive and negative ions are extracted in an alternating manner, introducing ultraviolet radiation to convert ozone in the plasma to active oxygen, the ultraviolet radiation being at a wavelength of 220 to 315 nm, whereby active oxygen is formed from the converted ozone, directing the extracted ions, the ozone, and the active oxygen to the contaminated object in the chamber and contacting the contaminated object with the extracted ions, the ozone, and the active oxygen to separate the microbes and infectious aerosols from the contaminated object and to decompose same, whereby the contaminated object is converted to a cleaned and disinfected object, the object being selected from a person, a clean room textile, a blanket, a medical textile, protective equipment, a parcel, and clothing.

2. A process according to claim 1, wherein the microbes and aerosols are electrically charged by the extracted ions and further comprising conducting the electrically charged microbes and aerosols through an electric field into a separation area or a plasma unit for decomposition.

3. The process of claim 1 wherein the chamber is further comprised of a conveyor on which the object contaminated with microbes and infectious aerosols is transported through the chamber during conversion of the object to a cleaned and disinfected object.

4. A process for cleaning and disinfecting a location having an environment contaminated with microbes and infectious aerosols comprising the steps of generating a plasma in an open chamber placed in the location of the contaminated environment, the open chamber being open to and receiving the contaminated environment, whereby microbes and infectious aerosols in the contaminated environment are received in the open, chamber, extracting ions from the plasma by generating alternating positive and negative pulse voltages in the plasma, whereby positive and negative ions are extracted in an alternating manner, introducing ultraviolet radiation to convert ozone in the plasma to active oxygen, the ultraviolet radiation being at a wavelength of 220 to 315 nm, whereby active oxygen is formed from the converted ozone, directing the extracted ions, the ozone, and the active oxygen to the contaminated environment in the open chamber and contacting the contaminated environment with the extracted ions, the ozone, and the active oxygen to separate the microbes and infectious aerosols from the contaminated environment and to decompose same, whereby the contaminated environment is converted to a cleaned and disinfected environment.

5. The process of claim 4 wherein the open chamber is sufficiently large to hold a person and wherein the contaminated environment further comprises a person.

6. The process of claim 4 wherein the contaminated environment is selected from an airplane cabin, a railroad car, a residence, a ship, a place where livestock is kept, a food handling facility, an industrial facility, a greenhouse, a warehouse where food is stored.

7. The process of claim 6 wherein the industrial facility is a semiconductor facility.

8. The process of claim 6, wherein the industrial facility is an optical products facility.

9. A process for cleaning and disinfecting a textile contaminated with microbes and infectious aerosols comprising the steps of:
    placing a contaminated textile on a plasma-generating device, the device being sized and dimensioned to have a textile placed over a body of the device, the body comprising nozzles, a plasma-generating electrode system located inside of the body, and a source of ultraviolet radiation located inside the body;
    generating a plasma in the device, the plasma being generated at a location in the device that does not provide direct exposure of the plasma to the textile;
    extracting ions from the plasma by generating positive and negative pulse voltages in the plasma, the positive and negative pulse voltages alternating with each other, whereby positive and negative ions are extracted in an alternating manner;
    generating ultraviolet radiation in the device to convert ozone in the plasma to active oxygen, the ultraviolet radiation being at a wavelength of 220 to 315 nm, whereby active oxygen is formed from the converted ozone;
    directing the extracted ions, the ozone, and the active oxygen through the nozzles to the contaminated textile on the device and contacting the contaminated textile with the extracted ions, the ozone, and the active oxygen to separate the microbes and infectious aerosols from the contaminated textile and to decompose same;
    whereby the contaminated textile is converted to a cleaned and disinfected textile, the textile being selected from a clean room textile, a medical textile, a blanket, protective equipment, and clothing.

\* \* \* \* \*